United States Patent [19]

Nagashima et al.

[11] 4,222,394
[45] Sep. 16, 1980

[54] SYSTEM FOR PROCESSING A WAVEFORM FOR A LARYNX STROBOSCOPE

[75] Inventors: Hironobu Nagashima, Tokyo; Koji Tuda; Masatoshi Marui, both of Fukuoka, all of Japan

[73] Assignee: Asahi Kogaku Kogyo Kabushiki Kaisha, Toyko, Japan

[21] Appl. No.: 960,515

[22] Filed: Nov. 13, 1978

[30] Foreign Application Priority Data

Nov. 14, 1977 [JP] Japan ............................ 52-152427[U]

[51] Int. Cl.³ ............................................... A61B 5/00
[52] U.S. Cl. ................................... 128/773; 179/1 SC
[58] Field of Search ............. 128/773, 630; 179/1 SC, 179/1 ST, 1 SA

[56] References Cited

U.S. PATENT DOCUMENTS

| | | | |
|---|---|---|---|
| 3,024,783 | 3/1962 | Timeke | 128/773 |
| 3,345,979 | 10/1967 | Miura et al. | 128/773 |
| 3,376,386 | 4/1968 | Fant | 179/1 SA |
| 3,450,989 | 6/1969 | Dickinson | 179/1 SC |
| 3,837,332 | 9/1974 | Meyers | 128/773 |

*Primary Examiner*—Lee S. Cohen
*Attorney, Agent, or Firm*—Sughrue, Rothwell, Mion, Zinn and Macpeak

[57] ABSTRACT

A device for processing a waveform for a larynx stroboscope having a plurality of filters receiving a vocal cord vibration signal. The outputs of the plurality of filters are automatically switched over by subjecting the outputs of the plurality of filters to comparision with one another to detect the fundamental wave component of the vocal cord vibration signal.

10 Claims, 3 Drawing Figures

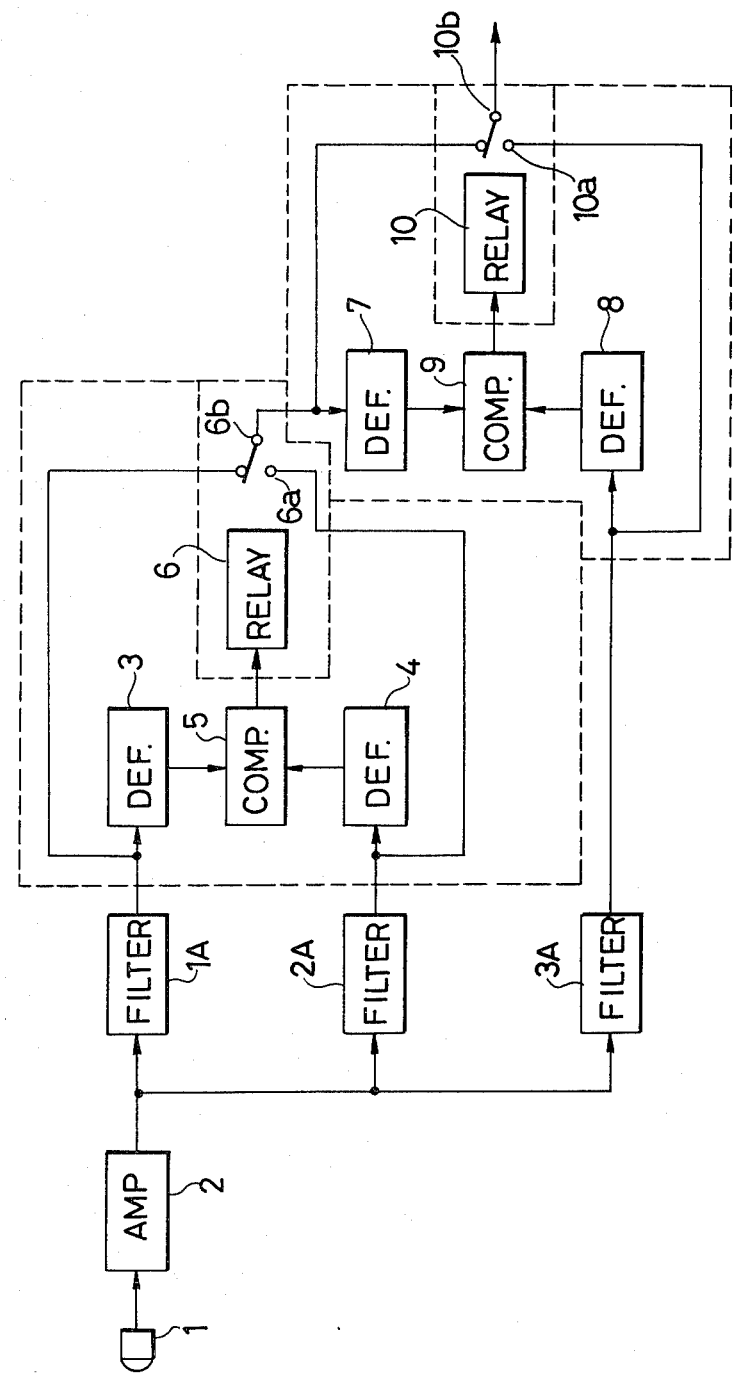
F I G. 1

SYSTEM FOR PROCESSING A WAVEFORM FOR A LARYNX STROBOSCOPE

BACKGROUND OF THE INVENTION

This invention relates to a device for processing a waveform in a larynx stroboscope adapted to observe vocal cords and diagnose problems in the vocal cords while making audible sounds.

A larynx stroboscope operates to cause a discharge tube to emit light in synchronization with the vibration of vocal cords making sounds and to apply the light to the vocal cords so that the observer can observe the vocal cords as if they were at rest. In order to precisely observe vocal cords being vibrated, it is necessary to receive the vocal cord vibration with a microphone to precisely detect the fundamental wave component included in the vocal cord vibration signal generated by the microphone. This allows the discharge tube to emit light in synchronization with the fundamental wave component. Stated differently, it is necessary to remove as much as possible of the harmonic wave components which obstruct the synchronous light emission of the discharge tube.

Different vocal cord vibration signals are of course detected from different persons by the microphone. In general, the vocal cord vibration signal includes a number of harmonic waves as well as the fundamental wave component. In a conventional larynx stroboscope, a vocal cord vibration signal detected by the microphone is applied to a filter, and the harmonic wave components of the vocal cord vibration signal are removed as much as possible by manually adjusting the frequency band of the filter. The operation can therefore extract the fundamental wave component of the vocal cord vibration signal, so that the discharge tube emits light in synchronization with the fundamental wave component thus extracted.

In this connection, it is emphasized that different vocal cord vibration frequencies are produced by different persons being examined. In addition, the same vocal cord vibration frequency is not always produced by the same person whenever he makes audible sounds. Accordingly, it is necessary for the operator to selectively adjust the frequency band of the filter whenever the vocal cord vibration frequency is changed. However, since the period of time for which the person to be examined can make continuous sounds is limited, the operator must carry out the selective adjustment of the frequency band of the filter. Thus, the operation of the conventional larynx stroboscope is troublesome and not efficient in terms of available examination time. Accordingly the operator cannot entirely devote himself to the observation and diagnosis of the vocal cords of a person to be examined.

SUMMARY OF THE INVENTION

Accordingly, an object of the invention is to eliminate the drawbacks accompanying a conventional larynx stroboscope.

Another object of this invention is to provide a device that permits the operator to devote himself to the observation and diagnosis of vocal cords.

These and other objects of this invention are accomplished by having a plurality of filters having different frequency bands provided in parallel. Even if the vocal cord vibration frequency of a person to be examined is changed, the fundamental wave component of the vocal cord vibration signal is automatically selected by automatically switching the outputs of the filters. Therefore, the prior art mode of operation where the frequency band of the filter is selectively adjusted in accordance with the vocal cord vibration frequency of a person to be examined can be completely eliminated. Accordingly, the operator can devote himself to the observation and diagnosis of the vocal cords.

This invention will be described with respect to the drawings and the preferred embodiment as follows.

BRIEF DESCRIPTION OF THE DRAWINGS

FIG. 1 is a block diagram showing a circuit embodying this invention; and

DESCRIPTION OF THE PREFERRED EMBODIMENT

Figure 2:
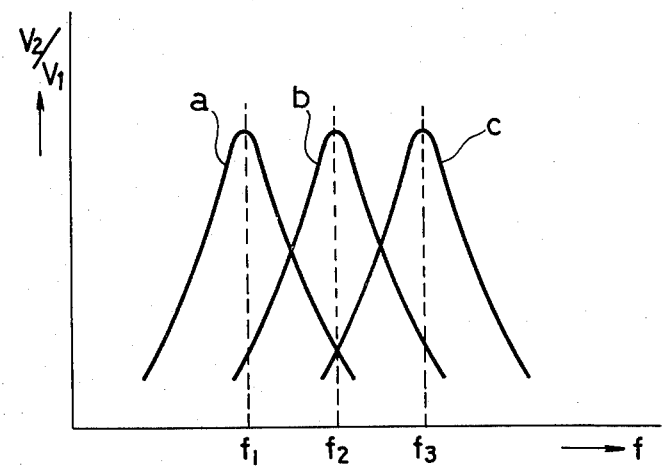
FIGS. 2 and 3 show the characteristic curves of filters employed in the circuit shown in FIG. 1.

One preferred embodiment of this invention will now be described with reference to the accompanying drawings, in which FIG. 1 is a block diagram showing a circuit in which the amplitudes of the outputs of three filters are subjected to comparison thereby to automatically detect the fundamental wave component of a vocal cord vibration signal. The circuit shown in FIG. 1 comprises a contact microphone 1 and an amplifier circuit 2 receiving the microphone output. Filters 1A, 2A and 3A are interposed between the amplifier 2 and amplitude detecting circuits 3, 4, 7 and 8. Comparator circuits 5 and 9 receive the detecting circuits' outputs. Relay circuits 6 and 10 have contact portions 6a and 10a with common terminals 6b and 10b, respectively.

The amplitude detecting circuits 3 and 4, the comparator circuit 5 and the relay circuit 6 form a first fundamental wave component detecting circuit 11. The amplitude detecting circuits 7 and 8, the comparator circuit 9 and the relay circuit 10 form a second fundamental wave component detecting circuit 12.

The filters 1A, 2A and 3A are band-pass filters whose characteristics are as shown in FIG. 2. The horizontal axis is frequency f and the vertical axis is the input/output voltage ratio $V_2/V_1$. In FIG. 2, reference character a indicates the characteristic curve of the filter 1A with the central frequency $f_1$, reference character b indicates the characteristic curve of the filter 2A with the central frequency $f_2$, and reference character c indicates the characteristic curve of the filter 3A with the central frequency $f_3$, such that $f_3 > f_2 > f_1$.

In operation, the contact microphone 1 is placed over the larynx to detect the vibration signal of vocal cords which are emitting audible sounds. The vocal cord vibration signal is amplified by the amplifier circuit 2. The output of the amplifier circuit 2 is applied to the filters 1A through 3A. The output of the filter 1A is applied to the amplitude detecting circuit 3, where the waveform amplitude is detected. Similarly, the output of the filter 2A is applied to the amplitude detecting circuit 4, where the waveform amplitude is detected. The outputs of the two amplitude detecting circuits 3 and 4 are used as inputs to the comparator circuit 5. The output of the comparator circuit 5 is at a logical low level when the output of the amplitude detecting circuit 3 is greater than the output of the amplitude detecting circuit 4. It is at a logical high level when the former is smaller than the latter.

When the output of the comparator circuit 5 is at the logical low level, the relay circuit 6 is not operated and the output of the filter 1A is connected to the common terminal 6b of the relay contact means 6a. When the output of the comparator circuit 5 is at the logical high level, the relay circuit 6 is operated and the output of the filter 2A is applied to the common terminal 6b of the relay contact means 6a. Hence, among the outputs of the filters 1A and 2A, the one of greater amplitude is obtained at the common terminal 6b.

The signal at the common terminal 6b is applied to the amplitude detecting circuit 7, where the amplitude of the signal is detected. The output of the detecting circuit 7 is compared with the output amplitude of the filter 3A detected by the amplitude detecting circuit 8 in the comparator circuit 9. The output of comparator 9 controls the operation of the relay circuit 10. Among the outputs of the filters 1A through 3A, the largest in amplitude is obtained at the common terminal 10b of the contact 10a of the relay circuit 10.

The vocal cord vibration signal contains the fundamental wave component largest in amplitude and the harmonic wave components. If the frequency of the fundamental wave component is in the vicinity of the frequency $f_1$ shown in FIG. 2, the output amplitude of the filter 1A is larger than the output amplitudes of the filters 2A and 3A which have pass bands higher than the frequency $f_1$ and pass the harmonic wave components. Therefore, the output of the filter 1A is obtained at the common terminal 10b of the relay contact 10a. The output of the filter 1A has a waveform in which, as is apparent from FIG. 2, the harmonic wave components are damped to a considerable extent when compared with the fundamental wave component. Thus, the fundamental wave component of the vocal cord vibration signal is automatically detected.

In the circuit described above, three filters are employed; however, the present invention is not limited thereto or thereby. That is, the number of filters may be, in general, n (n=1, 2, 3, ...). That is, n filters are provided, and the output of the amplifier circuit 2 is applied to the n filters. The outputs of the filters are subjected to comparison to obtain the fundamental wave component. In case of using n filters, the same circuit as the fundamental wave detecting circuit 12 is added to the circuit used when (n-1) filters are employed. The final output obtained when (n-1) filters are used and the output of the n-th filter are applied to the two amplitude detecting circuits of the newly added fundamental wave detecting circuit, respectively, so that among the outputs of the n filters, the one largest in amplitude is automatically obtained.

The final output is a wave-form which contains most of the fundamental wave component of the vocal cord vibration waveform with the harmonic wave components damped. The distortion of the final output can be reduced by increasing the number of filters, making the central frequencies closer to one another and improving the quality factor Q of the filters.

In the circuit described above, all the filters are band-pass filters; however, a low-pass filter may be used as the filter whose pass-band is the lowest. However, when the output of the low-pass filter is automatically selected as the final output, the harmonic wave components must be damped, and therefore it is necessary that the lower limit of the fundamental frequency of the vocal cord vibration signal to be detected is close to the cut-off frequency of the low-pass filter.

According to the experiments, when the fundamental frequency of the vocal cord vibration signal is high (higher than 400 Hz), in general it does not contain many harmonic wave components. Therefore, a high-pass filter may be employed as the filter whose pass-band is the highest. However, a band-pass filter should be used as the filter whose pass-band is between those of the low-pass filter and the high-pass filter, as in the above-described case.

Figure 3:
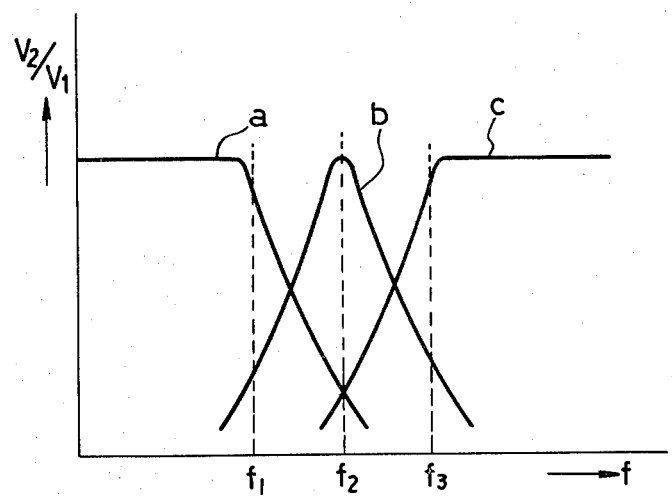

The filtering characteristic obtained when three filters are employed is as shown in FIG. 3, with the horizontal axis as frequency f and with the vertical axis as input/output voltage ratio $V_2/V_1$. In FIG. 3, reference character a indicates the characteristic curve obtained when a low-pass filter is employed as the filter 1A in FIG. 1, with the cut-off frequency $f_1$. Reference character b indicates the characteristic curve of the filter 2A in FIG. 1, with the central frequency $f_2$ and reference character c indicates the characteristic curve obtained when a high-pass filter is used as the filter 3A in FIG. 1, with the cut-off frequency $f_3$ ($f_3 > f_2 > f_1$).

As is clear from the above description, according to the invention, even if the frequency of the vocal cords of a partient is varied with time, it is automatically followed. Therefore, the synchronous condition is completely obtained at all times, which makes the operation of the larynx stroboscope device continuously stable. Thus, the vocal cords can be precisely observed and diagnosed.

It is apparent that modifications of the system are possible without departing from the essential scope thereof.

What is claimed is:

1. In a system for sensing a sound vibration signal having a fundamental wave component from a larynx, the system having sensor means for sensing sound vibrations from a larynx and amplifier means receiving the output of said sensor means and producing an amplified output, the improvement comprising: a plurality of at least two filter means each connected to and receiving the output of said amplifier means, first fundamental wave component detecting circuit means comprising first and second amplitude detecting means each connected to and receiving the output of a respective one of said filter means, comparator means connected to and receiving the outputs of said first and second amplitude detecting means, and switch means connected and responsive to the output of said comparator means for detecting the fundamental wave component of said larynx vibration signal.

2. The system of claim 1 wherein said plurality of filter means are disposed in a parallel arrangement to receive the output of said amplifier means.

3. The system of claim 2 wherein said filter means are band-pass filters having different center frequencies.

4. The system of claim 1 wherein said switch means comprises relay circuit means connected and responsive to the output of said comparator means for selectively switching from one state to another to deliver from said plurality of filter means the output thereof having the largest amplitude, whereby a first fundamental wave component is sensed.

5. The system of claim 4 further comprising at least third filter means disposed in parallel with said plurality of filter means to receive the output of said amplifier means, and second fundamental wave component detecting circuit means connected and responsive to the output of said switch means and said third filter means to detect the fundamental wave component of said larynx vibration signal.

6. The system of claim 5 wherein said second fundamental wave component detecting circuit means comprises third amplitude detecting means connected to and receiving the output of said third filter means, fourth amplitude detecting means connected to and receiving the output of said switch means, second comparator means connected to and receiving the outputs of said third and fourth amplitude detecting means, and second switch means connected and responsive to the output of said second comparator means to deliver an output of the fundamental wave component of said larynx vibration signal.

7. The system of claim 5 wherein said plurality of filter means and said third filter means are band-pass filters.

8. The system of claim 7 whrein said plurality of filter means and said third filter means have respective different band-pass ranges $f_1$, $f_2$ and $f_3$ and $f_3 > f_2 > f_1$.

9. The system of claim 5 wherein said plurality of filter means comprise a low-pass filter and a band-pass filter and said third filter means comprises a high-pass filter, said low-pass filter having a cut-off frequency $f_1$, said band-pass filter having a central frequency $f_2$ and said high-pass filter having a cut-off frequency $f_3$, wherein $f_3 > f_2 > f_1$.

10. The system of claim 5 wherein the number of said filter means is n, the number of fundamental wave component detecting circuit means is n-1, and n is an integer equal to or greater than 3.

* * * * *